(12) United States Patent
Cremer et al.

(10) Patent No.: US 8,425,521 B2
(45) Date of Patent: Apr. 23, 2013

(54) TENSIONING DEVICE FOR SURGICAL ELEMENTS

(75) Inventors: Axel Bernhard Cremer, Wiler b. Utzenstorf/BE (CH); This Aebi, Grenchen (CH)

(73) Assignee: Stryker Trauma AG (CH)

(*) Notice: Subject to any disclaimer, the term of this patent is extended or adjusted under 35 U.S.C. 154(b) by 170 days.

(21) Appl. No.: 13/014,052

(22) Filed: Jan. 26, 2011

(65) Prior Publication Data
US 2011/0196380 A1   Aug. 11, 2011

(30) Foreign Application Priority Data

Jan. 26, 2010   (DE) .................. 10 2010 005 706

(51) Int. Cl.
*B23B 31/20*   (2006.01)

(52) U.S. Cl.
USPC .............................. 606/86 R; 279/50; 279/51

(58) Field of Classification Search ............ 606/53, 606/86 B, 96, 97, 103, 104; 279/43–43.1, 279/46.1–46.2, 50–51; 81/438–439, 451–453; 433/127–129
See application file for complete search history.

(56) References Cited

U.S. PATENT DOCUMENTS

| | | | |
|---|---|---|---|
| 1,849,101 A * | 3/1932 | Livergood | 403/365 |
| 2,889,085 A | 6/1959 | Collins | |
| 3,975,032 A | 8/1976 | Bent et al. | |
| 4,091,880 A | 5/1978 | Troutner et al. | |
| 4,140,111 A | 2/1979 | Morrill | |
| 4,167,062 A * | 9/1979 | Page et al. | 433/129 |
| 4,441,563 A | 4/1984 | Walton, II | |
| 4,763,548 A | 8/1988 | Leibinger et al. | |
| 5,248,068 A | 9/1993 | Goergen et al. | |
| 5,312,410 A | 5/1994 | Miller et al. | |
| 5,478,093 A * | 12/1995 | Eibl et al. | 279/51 |
| 5,483,952 A | 1/1996 | Aranyi | |
| 5,496,327 A | 3/1996 | Den Ouden et al. | |
| 5,507,727 A | 4/1996 | Crainich | |
| 5,609,596 A | 3/1997 | Pepper | |
| 5,643,319 A | 7/1997 | Green et al. | |
| 5,888,200 A * | 3/1999 | Walen | 606/167 |
| 5,902,306 A | 5/1999 | Norman | |
| 5,921,563 A * | 7/1999 | Huggins et al. | 279/131 |
| 6,042,585 A | 3/2000 | Norman | |
| 6,132,435 A * | 10/2000 | Young | 606/104 |
| 6,415,693 B1 | 7/2002 | Simon et al. | |
| 6,689,140 B2 | 2/2004 | Cohen | |
| 7,066,940 B2 * | 6/2006 | Riedel et al. | 606/79 |
| 7,094,240 B2 | 8/2006 | Molz, IV et al. | |
| 7,219,581 B2 * | 5/2007 | Tulloch et al. | 81/112 |
| 7,771,429 B2 * | 8/2010 | Ballard et al. | 606/86 R |

(Continued)

FOREIGN PATENT DOCUMENTS

| | | |
|---|---|---|
| DE | 19945322 A1 | 5/2001 |
| DE | 102005058868 A1 | 3/2007 |
| WO | 9009150 A1 | 8/1990 |

*Primary Examiner* — Todd Manahan
*Assistant Examiner* — Eric S Gibson
(74) *Attorney, Agent, or Firm* — Lerner, David, Littenberg, Krumholz & Mentlik, LLP

(57) ABSTRACT

A tensioning device for surgical elements is described. The tensioning device comprises a fixation device, a clamping device, a spring device, and a force deflecting device that interacts with the clamping device. The force deflecting device is designed to convert the spring force exerted by the spring device on the clamping device into a clamping force exerted by the clamping device on the surgical element.

21 Claims, 2 Drawing Sheets

U.S. PATENT DOCUMENTS

| | | |
|---|---|---|
| 7,849,766 B2 | 12/2010 | Sharifi-Mehr et al. |
| 7,896,355 B2 * | 3/2011 | Wienhold ....................... 279/22 |
| 8,016,830 B2 * | 9/2011 | Veldman et al. ............ 606/86 R |
| 8,096,998 B2 | 1/2012 | Cresina |
| 8,104,774 B2 * | 1/2012 | Mosimann et al. ............. 279/51 |
| 2002/0072753 A1 | 6/2002 | Cohen |
| 2003/0130663 A1 * | 7/2003 | Walen ............................ 606/80 |
| 2005/0149086 A1 | 7/2005 | Huxel et al. |
| 2007/0171540 A1 * | 7/2007 | Veldman et al. .............. 359/680 |
| 2008/0246233 A1 * | 10/2008 | Wienhold ....................... 279/82 |
| 2009/0192517 A1 * | 7/2009 | Miletto et al. ................. 606/104 |
| 2009/0234365 A1 * | 9/2009 | Gross ........................... 606/104 |

* cited by examiner

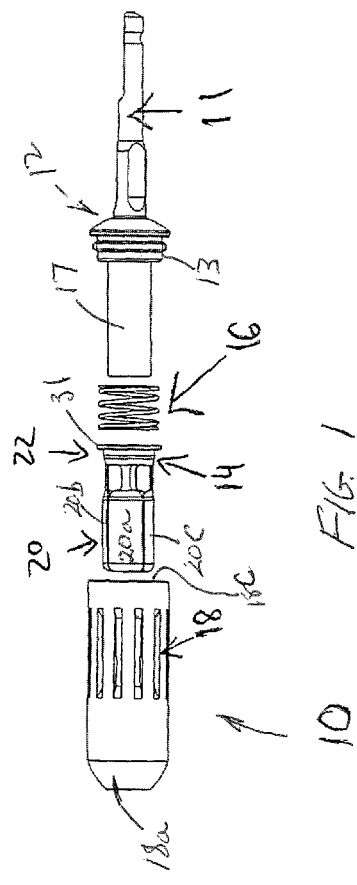

TENSIONING DEVICE FOR SURGICAL ELEMENTS

BACKGROUND OF THE INVENTION

Surgical elements such as bone screws are used in various ways, such as in external fixation systems. Currently in order to insert or drive the screws into a bone, tool couplers that vary according to the screw diameter with suitable tensioning devices are used. This is cumbersome to the extent that in any given fixation situation, varying screw diameters are typically used (e.g. knee bridging—in the femur: 6 mm screws; in the tibia: 5 mm screws).

The current couplers must be opened and closed by hand. Despite this, there is often some noticeable play in the screws in the tensioning device. This leads, above all when driven by a power tool, to the undesirable decoupling of the tensioning device and screw even a flinging of the screw into the air.

For example, DE 10 2005 058 868 A1 shows a screwdriver for bone screws that has a gripping part and a shaft that is fastened to it in a torque-proof manner. The free end of the shaft has a non-rounded cross-section and may be inserted in a form-fitting manner into the retainer opening in a head of a bone screw. In order to insert the free end of the shaft in the retainer opening of the bone screw, a grip sleeve must be moved in an axial direction, whereby a helical spring is tensed. This causes a bar to be moved in a longitudinal slit in the shaft in the direction of the gripping part, and retained completely in the grip casing. After the shaft is inserted into the retainer opening, the grip sleeve is once again released by the operator, so that under the effect of the unwinding spring, the bar is moved in the direction of the free end and due to a sliding surface is pushed radially outward against the inner wall of the retainer opening.

DE 199 45 322 A1 describes a chuck for a surgical drilling device. In order to insert a drill wire into the chuck, it is fed through a bore into the end surface of a guide element and on through a passage bore of a jaw guide. The drill wire then hits sliding surfaces of clamping jaws tensed by a leaf spring and thus spreads the clamping jaws outward in a radial direction. The pre-tensed clamping jaws are carried in an axial direction until they hit a supporting element projection with their jaw ends. In a final position, then the clamping surfaces of the jaws are entirely on the drill wire, so that the clamping jaws and the drill wire are clamped together.

BRIEF SUMMARY OF THE INVENTION

The tensioning device for surgical elements of the present invention comprises a fixation device that is designed for the torque-proof fixation of a surgical element, a clamping device that is designed to exert an essentially inward radial clamping force on the surgical element, a spring device that is designed to exert a spring force on the clamping device. The spring force is exerted in an essentially axial direction, and a force deflecting device that interacts with the clamping device, which is designed to convert at least part of the spring force exerted on the clamping device into at least a part of the clamping force exerted on the surgical element. The clamping device and the fixation device may be realized as separate structural elements or integrated into a single structural element.

The clamping device may have a contact surface for the surgical element, which, when the surgical element is inserted into the tensioning device, causes the clamping device to be moved against the spring force. In this manner, clamping force may be applied or increased. An increase in clamping force is then possible, for example, if the clamping device already has its own share of clamping force.

The clamping device may be constructed in an essentially rotation-symmetrical manner. The clamping device may include one or more deflectable clamp fingers. If several clamp fingers are provided, these may surround the surgical element in a circumferential direction. The clamp fingers may, in such circumferential direction, be placed at equal intervals from one another.

The clamp fingers may have a first slanted surface that, by interacting with the surgical element, produces a radial outward deflection of the clamp finger. This first slanted surface may correspond to the above-cited contact surface.

The force deflection device may include a second slanted surface, against which the clamping device is or can be pretensed by means of a spring device. Several second slanted surfaces may be provided (for example, at intervals). It is also possible for the second slanted surface to have a rotation-symmetrical and/or conical form. If the clamping device also has a rotation-symmetrical form or it surrounds the surgical element in at least the circumferential direction, the element may be stabilized so that there is no play, so that the known decoupling can be prevented.

The clamping device may include at least one third slanted surface that interacts with the minimum of one second slanted surface of the force deflecting device in such a way as to deflect force. Thus it is possible, for example, for a third slanted surface to be provided on each clamp finger. For the person skilled in the art, it is obvious that for the force deflecting function, in principle a single slanted surface is sufficient. So, for example, only the second slanted surface may be provided for the force deflecting device, and the third slanted surface in the area of the clamping device may be replaced by a differently-shaped contact surface or even by a contact surface in the form of a line.

The fixation device may have an opening to receive a part of the surgical element. For example, a distal part of the surgical element may be retained in the opening of the fixation device. The terms distal or proximal within the context of this publication refer to a direction away from the operator's position or toward the operator's position.

The opening of the fixation device may be provided with a profile that allows a torque-proof (preventing relative rotation) connection with a surgical element provided with a complementary profile. The profile may, for example, take the form of a polygonal profile, such as, for example, a square or hexagon.

It is also possible for the opening of the fixation device to have several sections spaced at intervals from one another in an axial direction and tapering in a distal direction (for example, stepped). Such a design of the opening allows the torque-proof retention of surgical elements of varying diameters. In general the external diameters of the surgical elements may be in the range of several millimeters (e.g. from approximately 1 to approximately 10 mm).

The tensioning device may also include a casing part, which at least partially surrounds the clamping device on the outside. The force deflecting device may be arranged on the casing part (for example on a distal section of the casing part). Furthermore, a stop may be designed on the casing part against which the clamping device is or may be tensed through springs in the initial position.

Furthermore, the tensioning device may include a base body in which the fixation device is designed. On the base body there may also be a counter bearing for the spring device. In addition or alternatively to this, the casing part may be coupled to the base body. The coupling may be in such a way that a pre-set or settable axial relative position between the casing part and the base body is assured. This axial relative position may define the pre-tensing of the clamping device (and thus the clamping force) in the initial position, i.e. before receiving a surgical element. Suitable coupling mechanisms include, for example, screw connections, latch connections and the like.

According to a further form, a coupling device for coupling with a surgical tool or a tool hand grip may be provided on the base body. The surgical tool may be a surgical power tool (such as, for example, a battery-powered screwdriver).

Also proposed is a surgical tool that comprises the tensioning device. Aside from this, a surgical system is described, which comprises this surgical tool as well as several surgical elements to be tensed with varying external diameters. The surgical elements may include, for example, bone screws, threadless bone pins, borers, Kirschner wires (with and without thread), etc.

The surgical system may also include at least one frame element (for example a rod) of an external fixator. In such case, the surgical elements may be designed for the attachment of at least one frame element to a bone.

A tensioning device for inserting surgical elements into bone has an axially extending body portion having a drive shaft section at a first body portion end and a hollow shaft section adjacent a second body portion end and first and second axially spaced circumferential stop surfaces intermediate the first and second ends. The first stop surface being closer to the first body portion end and the second stop surface being closer to the second body portion end with the stop surfaces extending transversely to a longitudinal axis of the body portion. A clamping element is provided which has a plurality of deflectable gripping elements at a gripping end thereof and a mounting portion slidably engaging an outer surface of the hollow shaft section of the body portion. A biasing element is mounted on an outer surface of the hollow shaft section at a location thereon closer to the body portion first end than the clamping element. A first end of the biasing element engages the second circumferential stop surface and the clamping element mounting portion at a second biasing element end. A deflector surrounds the clamping and biasing elements and is fixedly mounted on an outer surface of the hollow shaft portion. The deflector has a first end engaging the first stop surface and a second end defining a surgical element receiving opening and has inner surfaces angled toward the longitudinal axis and toward the surgical element receiving opening. The angled surfaces of the deflector are engagable with outer surfaces of the deflectable gripping elements of the clamping element. The tensioning device deflector has an inner surface extending transverse to the longitudinal axis for engaging a stop element on the clamping element. Wherein the tensioning device shaft section includes a plurality of different size sequential recesses with the size of each recess increasing on moving from the first end towards the second end of the body portion. The bores are adapted to receive a drive end of a bone pin or a bone screw or other surgical elements.

BRIEF DESCRIPTION OF THE DRAWINGS

Additional specifics, advantages and aspects of the tensioning device described here for surgical elements may be seen from the following drawings. These show:

FIG. 1 is an exploded view of an embodiment of a tensioning device for surgical elements;

FIG. 2 is a sectional view of the tensioning device for surgical elements in the initial position according to FIG. 1.

DETAILED DESCRIPTION

Figure 3:
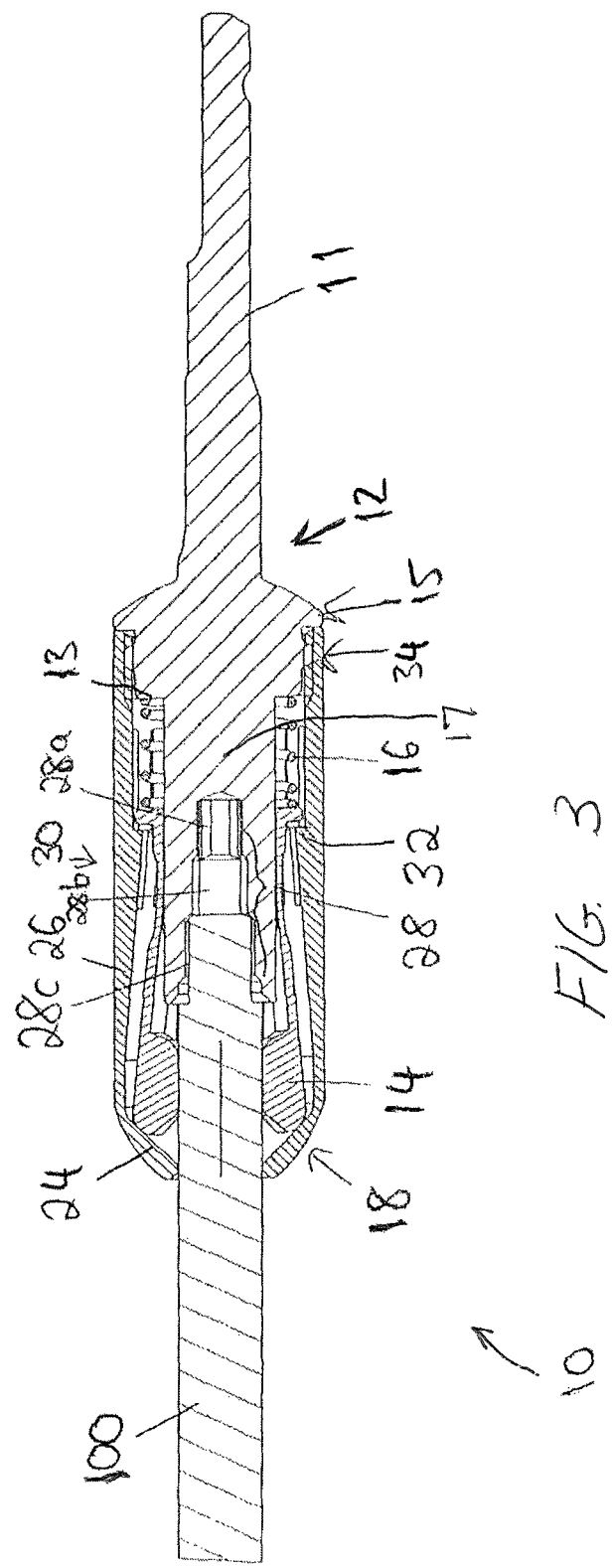
FIG. 3 is a sectional view of the tensioning device for surgical elements according to FIG. 1, whereby an end portion of a surgical element is clamped in the tensioning device.

Corresponding elements in the figures are identified with the same references. The words "front side" and "back side" refer to the orientation of the tensioning device in the figures. It is understood that in operation, the tensioning device may be oriented as desired.

FIG. 1 shows an exploded view of essential structural components of a tensioning device generally denoted as 10 for clamping of surgical instruments such as, for example, bone screws, bone borers, bone pins or Kirschner wires. The tensioning device 10 comprises a base body 12 including a back shaft section 11 and a front shaft section 17, a clamping device 14, a spring or biasing device 16 and a force deflecting device 18 that is designed as a casing part. These structural components are each rotation-symmetrical.

The base body 12 is shaped as a one-piece, cylindrical shaft extending along a longitudinal axis 9 (FIG. 2), which is equipped on the front section 17 to receive the clamping device 14, the spring device 16 and the surgical elements, and on the back side for coupling with a surgical (power) tool in the form of, for example, a drive shaft. For this purpose, the back section of the shaft section 11 has two-dimensional segments for the torque-proof or torque transmitting coupling onto the surgical tool, which transfers a rotational movement to the shaft.

As may be seen in the sectional view according to FIG. 2, a rotation-symmetrical circumferential projection 15 is arranged near the center of the base body 12, which, on its front surface, forms a counter bearing 13 for the spring device 16. The spring device 16 in this embodiment is designed as a helical spring, which fits precisely over the front section 17 of the base body 12, and in the back has an end which is pushed up to the stop surface on the counter bearing 13.

The clamping device 14 is designed as a one-piece hollow-cylindrical collet chuck, whereby the collet chuck has four clamp or gripping fingers 20a-20d (in FIG. 1 only three fingers (20a, 20b and 20c) are visible due to the perspective view with 20d not shown), whereby the four clamp fingers are each connected by means of a narrow bridge to a hollow-cylindrical base element 22 of device 14. The fingers or gripping elements may be separated by narrow slits. The clamping device 14, in connecting to the helical spring 16, is placed over the front section 17 of the base body 12, until an end flange 31 of the base element 22 touches the helical spring 16. This way the helical spring 16 can be clamped between the base element 22 of the clamping device 14 and the counter bearing surface 13 of the base body 12.

The force deflecting device 18 designed as a casing part which may be cylindrical, whereby the force deflecting device 18 is conically tapered on the front side 18a. The force deflecting device 18 has an opening 18b on its front side and an opening on a back end 18c, as well as a hollow space inside to receive the clamping device 14 and the spring device 16. In assembling the tensioning device 10, the force deflecting device 18 is fitted over the helical spring 16 and clamping device 14 mounted on the front of the base body 12. Then the back end 18c of force deflecting device 18 is fastened to the projection 15 preferably using a screw connection.

The force deflecting device 18, together with the stepped projection 15 of the base body 12, forms a protective casing for the tensioning device 10, whereby the projection 15 forms the bottom of the casing and the force deflecting device 18 forms a sleeve- and cover surface as shown in FIG. 2.

FIG. 2 makes clear the interaction of the various structural elements. Here, the design of the inner surfaces of the force deflection device 18 take on major significance. This comprises, on its front 18a inner side, a conical slanted surface 24, which extends in annular form, and is tapered inwardly toward end 18a and axis 9, up to front opening of the force deflecting device 18. A second slanted surface 26 is provided which connects directly to the first slanted surface 24 and tapers conically towards axis 9 on moving towards the back end 18c of the force deflecting device 18. The second slanted surface 26 ends in gradation or step 32 that extends in a radially inward direction, which serves as an attachment element and a stop for the clamping device 14 which, in an assembled condition, can be moved away from step 32 towards surface 13 in an axial direction. The clamping device 14 in its basic condition shown in FIG. 2 (i.e. without being stocked with a surgical element), is pre-tensed against the gradation or step 32 by the spring device 16. The pre-tensioning force is defined by the axial relative position of the base body 12 and the force deflecting device 18.

As already explained, the clamping device 14 has four clamp fingers 20a, 20b, 20c and 20d, whose front inner surfaces each include two inner rounded or slanted surfaces 21a, 21b slanted in a circumferential direction. The two slanted surfaces 21a and 21b are designed in such a way that the four clamp fingers 20a, 20b, 20c and 20d, which are arranged toward each other circumferentially around the clamping device 14, form, on their front side, a double-conical or double-funnel retainer opening, in which the surgical element may be pushed for attachment and then pulled out to remove. The clamp fingers 20a, 20b, 20c and 20d can mainly be deflected in a radially outwardly direction. The clamp fingers 20a, 20b, 20c and 20d are characterized by a low spring constant so that surgical elements, even those with larger diameters can be pushed in with less effort. This is achieved by means of proper selection of materials for the clamping device 14.

The respective outer side of the clamp finger 20 has on its front end a slightly slanted surface 21c, which is rounded in an axial direction and ends in an outer surface, whereby the respective outer sides 21d of the clamp fingers 20 are also rounded in a circumferential direction.

The base body 12, on its front end, comprises a fixation device 28, which is designed as a series of concentrically arranged recesses 28a, 28b, 28c in the cylindrical shaft 17. The recess thus comprises three sections 28a, 28b and 28c that are spaced from one another in an axial direction and taper in a distal direction, which, as shown in FIG. 3, are provided for the torque-proof (non-rotational) retaining of a surgical element 100. The three sections each preferably have a square profile with varying diameters, in which an attachment pin of a surgical element with a corresponding diameter with a complementary square profile may be inserted in a torque-locking (non-rotational) manner.

The three diameters of fixation device 28 (28a, 28b and 28c described here are designed to receive screws with diameters of 4 mm, 5 mm and 6 mm respectively. It is understood that this publication is not limited to the diameters mentioned here. In order to assure access to the recess for all screw sizes, the segments of the recesses are arranged in order of size, beginning with the largest diameter on the front end of the base body (28c). Here it is advantageous that the smallest diameter 28a is farthest to the back, since a more stable retention is thus assured.

In the assembled condition, the clamping device 14 is pre-tensioned in the tensioning device 10 by the spring device 16 in an axial direction as well as by the force deflecting device 18 in a radial direction. The clamping in an axial direction is effected by the spring device 16 through the fact that the spring device 16 inserted on the front end 17 of the base body 12 is pressed together between the counter bearing 13 of the base body 12 and end flange 31 of base 22 of the clamping device 14. Thus the axial motion of the clamping device 14 toward the front is limited by the engagement of the front surface of flange 31 and ledge or step 32 of the force deflecting device 18.

The radial pre-tensioning of the clamp fingers 20a, 20b, 20c and 20d, on the other hand, is effected by means of the guiding or deflection of the clamp fingers 20a, 20b, 20c and 20d along the front slanted surfaces 24 of the force deflecting device 18. Thus the tensioning device 10 described essentially comprises two tensioning mechanisms (helical spring on the one hand, and on the other, clamp fingers 20a, 20b, 20c and 20d that are pre-tensed in a radially inward direction), which tensioning mechanisms are serially connected to one another.

In order to achieve a better understanding of the functioning of the tensioning device 10 described here, FIG. 3 shows the tensioning device 10 equipped with the surgical element 100. The element 100 is inserted manually through the front opening 18b in the deflecting device 18 of tensioning device 10. The diameter of the surgical element 100 (which is greater than the opening made by the clamp fingers 20a, 20b, 20c and 20d which are tensed radially inward), the clamp fingers 20a, 20b, 20c and 20d are pressed axially toward the back and radially outward, whereby the clamp fingers 20a, 20b, 20c and 20d are guided along the conical slanted surfaces 24 of the force deflecting device 18.

The clamp fingers 20a, 20b, 20c and 20d may open only if at the same time the whole clamping device 14 is moved by the insertion motion in an axial direction backward against the spring force of the spring device 16. Due to the resulting further compression of the spring device 16, its pre-tensioning is further increased, which, in turn (due to the force deflection by the force deflecting device 18) leads to an additional force exerted in a radial direction on the surgical element 100, as soon as the expansion of the clamp fingers 20a, 20b, 20c and 20d is great enough, in order to allow for the surgical element to pass in the direction of the fixation device recesses 28a, 28b and 28c. After completing the form-fitting insertion into one of the recesses 28a, 28b and 28c of the fixation device 28, the surgical element 100 is held in the tensioning device 10 solely by forces in the area of the clamp fingers 20a, 20b, 20c and 20d.

The axially-directed spring force of the spring device 16 is thus transformed on the clamp fingers 20a, 20b, 20c and 20d into a force exerted radially inward by the interaction of the slanted surface 24 of the force deflection device 18 with the respective clamp fingers 20a, 20b, 20c and 20d. In this way, the surgical element 100 is force-fit clamped in the tensioning device 10. Due to the interaction of the slanted surface 24 under pre-tensioning with the clamp fingers 20a, 20b, 20c and 20d and the surgical element 100 held by them, it is also centered and retained in the tensioning device 10 without play. For this reason, the surgical element 100 does not undergo any loosening or wobbling motion when it is rotated.

A further advantage of this embodiment is that the surgical element 100 may be clamped and then removed without additional structure (fixation screws, levers, etc.). In addition, the clamping device 14 serves exclusively for the fixation and centering of the clamped element 100, while the transfer of rotational motion to the surgical element 100 is carried out by the form-fitting connection of the fixation device 28 (recesses 28a, 28b and 28c) in the base body 12. This functional separation allows for separate optimization of the respective functions.

For example, the tensioning device 10 may accept, by turns, bone screws with 4 mm, 5 mm and 6 mm diameters. The concentration on the sizes 4, 5 and 6 mm is because these screws (e.g. Apex® screws, Apex Tool Group LLC) may be used in Stryker's external fixator systems (Hoffmann II, Hoffmann Xpress). The tensioning device 10 must be attached to the tool only once, after that, outside of pushing in and pulling out the bone screws, no further activation and, in particular, no change of the tensioning device 10 is required for bone screws with varying diameters.

Overall, the measures proposed herein lead to a reduction in the duration of the operation, the probability of erroneous manipulations, the probability that bone screws will fall out of the drive device and the risk of confusion among couplings or tensioning devices equipped with them. Furthermore, simple disassembly of the tensioning device 10 is possible due to the screw connection between the deflection device 18 and the base body 12. This facilitates sterilization and cleaning.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tensioning device for surgical elements comprising: a fixation device, designed for the torque-proof fixation of a surgical element mounted in a surgical element receiving opening therein which extends along a longitudinal axis;
   a clamping device, designed for the exertion of an essentially radial inward clamping force on the surgical element;
   a spring device, which works to exert spring force on the clamping device, whereby the spring force is essentially exerted in an axial direction; and
   a force deflecting device that interacts with the clamping device, which is designed to convert at least a part of the spring force exerted on the clamping device into at least part of the clamping force exerted on the surgical element, the force deflecting device having inner surfaces angled towards the surgical element receiving opening, wherein one of said angled inner surfaces is angled towards the longitudinal axis and another of said angled inner surface is angled away from the longitudinal axis, the angled inner surfaces of the force deflecting device engageable with the clamping device.

2. The tensioning device as claimed in claim 1, whereby the clamping device has a contact surface for the surgical element, such that when the surgical element is inserted into the tensioning device, it can be moved against the spring force.

3. The tensioning device as claimed in claim 1, whereby the clamping device comprises at least one clamp finger that can be deflected in a radial direction.

4. The tensioning device as claimed in claim 3, whereby a plurality of clamp fingers are provided, wherein the fingers surround the surgical element in its circumferential direction.

5. The tensioning device as claimed in claim 3, whereby the contact surface is designed as a first slanted surface on the at least one clamp finger, in order to produce a force component on the clamp finger radially outward.

6. The tensioning device as claimed in claim 5, whereby the force deflecting device comprises at least one second slanted surface, against which the clamping device is or can be pre-tensioned by means of the spring device.

7. The tensioning device as claimed in claim 6, whereby the second slanted surface has a conical shape.

8. The tensioning device as claimed in claim 7, whereby the clamping device comprises at least one third slanted surface, which interacts with the at least one second slanted surface of the force deflecting device in such a way as to produce a deflection force.

9. The tensioning device as claimed in claim 1, whereby the fixation device has a recess to receive a part of the surgical element, and whereby the recess is provided with a profile that allows a torque-proof coupling with the surgical element having a complementary profile.

10. The tensioning device as claimed in claim 9, whereby the recess has several segments spaced at intervals from each other in an axial direction and tapering in a distal direction, for the torque-proof retaining of surgical elements of varying diameters.

11. The tensioning device as claimed in claim 1, further comprising a casing part, which at least partially surrounds the clamping device from the outside.

12. The tensioning device as claimed in claim 11, whereby the force deflecting device is arranged on the casing part.

13. The tensioning device as claimed in claim 11, whereby a stop is arranged on the casing part, against which the clamping device in its initial position is or can be pre-tensed with a spring.

14. The tensioning device as claimed in claim 11, further comprising a base body, in which a fixation device is arranged.

15. The tensioning device as claimed in claim 14, whereby a counter bearing for the spring device is arranged on the base body.

16. The tensioning device as claimed in claim 14, whereby the casing part is coupled with the base body assuring a pre-set or settable axial relative position.

17. The tensioning device as claimed in claims 14, whereby the base body has a coupling device for coupling with a surgical tool, particularly a surgical power tool or a tool hand grip.

18. A tensioning device for inserting surgical elements into bone comprising: an axially extending body portion having a drive shaft section at a first body portion end, a hollow shaft section adjacent a body portion second end and first and second axially spaced circumferential stop surfaces intermediate the first and second ends, the first stop surface closer to the first body portion end and the second stop surface closer to the second body portion end, the stop surfaces extending transversely to a longitudinal axis of the body portion;
   a clamping element having a plurality of deflectable gripping elements at a gripping end thereof and a mounting portion slidably engaging an outer surface of the hollow shaft section of the body portion;
   a biasing element mounted on an outer surface of the hollow shaft section at a location thereon closer to the body portion first end than the clamping element, a first end of the biasing element engaging the second circumferential stop surface and the clamping element mounting portion at a second biasing element end;

a deflector surrounding the clamping element and the biasing element fixedly mounted on an outer surface of the hollow shaft portion and having a first end engaging the first stop surface and a second end defining a surgical element receiving opening and having inner surfaces angled towards the surgical element receiving opening, wherein one of said angled inner surfaces is angled towards the longitudinal axis and another of said angled inner surface is angled away from the longitudinal axis, the angled inner surfaces of the deflector engageable with outer surfaces of the deflectable gripping elements of the clamping element.

19. The tensioning device as set forth in claim 18 wherein the deflector has an inner surface extending transverse to the longitudinal axis for engaging a stop element on the clamping element.

20. The tensioning device as set forth in claim 18 wherein the hollow shaft section includes a plurality of different size sequential recesses with the size of each recess increasing on moving from the first end towards the second end of the body portion.

21. The tensioning device as set forth in claim 20 wherein each recess includes means for preventing the rotation of a surgical element mounted within the recess.

* * * * *